United States Patent
Graumann

(10) Patent No.: US 9,351,696 B2
(45) Date of Patent: May 31, 2016

(54) METHOD AND DEVICE FOR ESTABLISHING OBJECT DATA

(71) Applicant: SIEMENS AKTIENGESELLSCHAFT, Munich (DE)

(72) Inventor: Rainer Graumann, Hoechstadt (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 164 days.

(21) Appl. No.: 14/227,080

(22) Filed: Mar. 27, 2014

(65) Prior Publication Data

US 2014/0294160 A1    Oct. 2, 2014

(30) Foreign Application Priority Data

Mar. 27, 2013    (DE) .................. 10 2013 205 501

(51) Int. Cl.
*A61B 6/00*    (2006.01)

(52) U.S. Cl.
CPC .............. *A61B 6/505* (2013.01); *A61B 6/5235* (2013.01); *A61B 6/583* (2013.01)

(58) Field of Classification Search
CPC ......... A61B 6/583; A61B 6/582; A61B 6/585
See application file for complete search history.

(56) References Cited

U.S. PATENT DOCUMENTS

| | | | |
|---|---|---|---|
| 5,216,700 A | 6/1993 | Cherian | |
| 2004/0103903 A1 | 6/2004 | Falahee | |
| 2004/0171986 A1 | 9/2004 | Tremaglio, Jr. et al. | |
| 2008/0039866 A1 | 2/2008 | Stetz et al. | |
| 2009/0238341 A1* | 9/2009 | Kawamura | A61B 6/04 378/162 |
| 2011/0218546 A1 | 9/2011 | De La Fuente Klein et al. | |
| 2012/0106716 A1* | 5/2012 | Herrnsdorf | A61B 6/08 378/205 |
| 2014/0270067 A1* | 9/2014 | Clark | A61B 19/54 378/62 |

FOREIGN PATENT DOCUMENTS

| | | |
|---|---|---|
| CN | 102688099 A | 9/2012 |
| DE | 102008052680 A1 | 4/2010 |
| WO | 2004069061 A1 | 8/2004 |

* cited by examiner

*Primary Examiner* — Hoon Song
(74) *Attorney, Agent, or Firm* — Laurence Greenberg; Werner Stemer; Ralph Locher

(57) ABSTRACT

A method establishes a spatial position of a part of an x-ray ruler imaged in at least one x-ray image. The X-ray ruler is attached to an alignment of an object to be x-rayed. The X-ray ruler has at least a first part and a second part each having x-ray markers, and the first and second parts are connected to each other by a connection element. A spatial configuration of the x-ray markers is determined on a basis of images of the x-markers in an x-ray image or x-ray images.

9 Claims, 4 Drawing Sheets

FIG 4
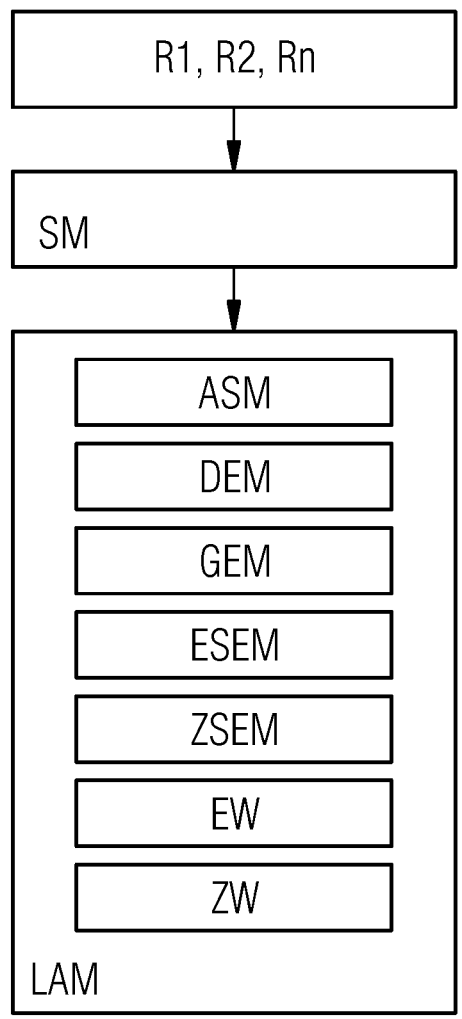
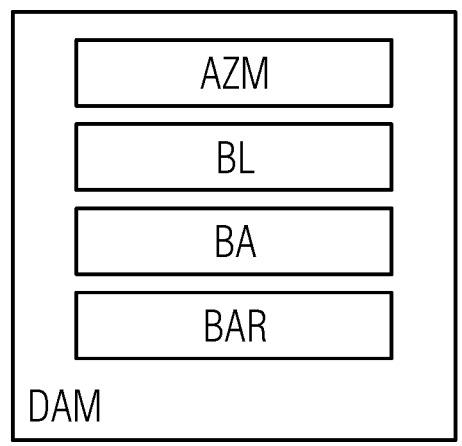

METHOD AND DEVICE FOR ESTABLISHING OBJECT DATA

CROSS-REFERENCE TO RELATED APPLICATION

This application claims the priority, under 35 U.S.C. §119, of German application DE 10 2013 205 501.3, filed Mar. 27, 2013; the prior application is herewith incorporated by reference in its entirety.

BACKGROUND OF THE INVENTION

Field of the Invention

The invention relates to a device and a method for establishing object data.

Due to restricted geometries in x-ray detectors, a plurality of x-ray recordings often have to be made for imaging relatively large regions of the body for the purposes of a diagnosis, a pre-surgical planning phase or an intraoperative progress or quality control. An example for this could lie in imaging the spinal column, an arm or a leg. The treating medical practitioner derives further work steps from these x-ray recordings. By way of example, in order to obtain overview images from several x-ray recordings, the individual x-ray recordings have to have a large-scale overlap in order to be able to relate these to one another. Prominent points or structures are selected in the overlapping, preferably parallax-free regions of two x-ray recordings and related to one another. However, for an overview image, this procedure is only expedient in the case of objects lying flat on the table. If the patient cannot be positioned flat on the table, there are distortions or foreshortenings of the imaged elements in the x-ray recordings. A diagnosis based on an overview image can only be undertaken taking into account the aforementioned imaging errors. However, in addition to high computational outlay, overlapping x-ray images entail an increased x-ray exposure of the patient. Moreover, associated prominent structures in the x-ray recordings are related using computationally intensive correlation methods since there often are only a few prominent structures or features in the overlapping regions that can be related unambiguously.

SUMMARY OF THE INVENTION

The invention is based on the object of specifying a device and an associated method for establishing object data.

In the following text, a device and a method for establishing the spatial position of a section of an x-ray ruler, which is formed from at least two parts, can be angled, and is imaged in at least one x-ray image, are described. The parts are connected by a connection element. The x-ray ruler, which contains at least a first and second part, which is provided with x-ray markers, and which can be angled, is attached to the alignment of an object to be x-rayed. By a position determination module for determining the spatial arrangement of the x-ray markers, object data are calculated on the basis of the images of the x-ray markers in the x-ray image or x-ray images. These object data can form the basis for establishing anatomical values such as e.g. leg length or leg axis.

The invention harbors the advantage that the spatial alignment of an object to be x-rayed can be established since the alignment and position of the x-ray ruler in space can be established.

The invention harbors the advantage that, e.g. a leg axis, leg length and/or a leg rotation can be established, even in the case of an angled position of the leg.

In addition to exact establishment of object data, the device and the associated method harbor the advantage that x-ray images to be combined to form an overview image can be aligned and/or strung together without there being overlapping regions in the individual x-ray images.

The invention harbors the advantage that it is also possible to spatially relate non-overlapping x-ray images.

The invention harbors the advantage that x-ray images only need to be made of surgically significant regions and the x-ray exposure of the patient is reduced further.

The invention harbors the advantage that the individual x-ray images can be aligned along an axis connecting these and at the distances therebetween.

In accordance with an added feature of the invention, a segmentation module is provided for segmenting the x-ray markers.

In accordance with another feature of the invention, a representation module is provided for combining the x-ray images to form an overview image and for a spatial reconstruction of the x-ray ruler on a basis of the spatial configuration of the x-ray markers. The representation module is provided with submodules for displaying an object length, an object alignment and axis profiles of the object and/or of parts of the object.

In accordance with an additional feature of the invention, angle sensors are disposed in the connection element.

In accordance with a first mode of the invention, the x-ray images are combined to form an overview image. Furthermore an object length, an object alignment and axis profiles of the object and/or of parts of the object are determined due to the spatial arrangement of the x-ray markers.

Other features which are considered as characteristic for the invention are set forth in the appended claims.

Although the invention is illustrated and described herein as embodied in a method and a device for establishing object data, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 4 is an illustration of submodules.

DETAILED DESCRIPTION OF THE INVENTION

Using the method and the associated device, in particular the embodiment of an x-ray ruler, it is possible to query or determine a first angle emerging between parts of an x-ray ruler which can be angled by evaluating the x-ray markers of the x-ray ruler RL imaged in individual x-ray images. A second angle emerging by a tilt of the x-ray ruler RL with respect to a base is established by evaluating a size and orientation of the x-ray markers in the respective x-ray images.

In order to establish the object data, the x-ray ruler RL, which can be angled and is formed from at least two parts, is proposed. The parts of the x-ray ruler RL are connected by a connection element S. At least a first type of first x-ray markers is integrated into the x-ray ruler along the whole x-ray ruler.

Figure 1:
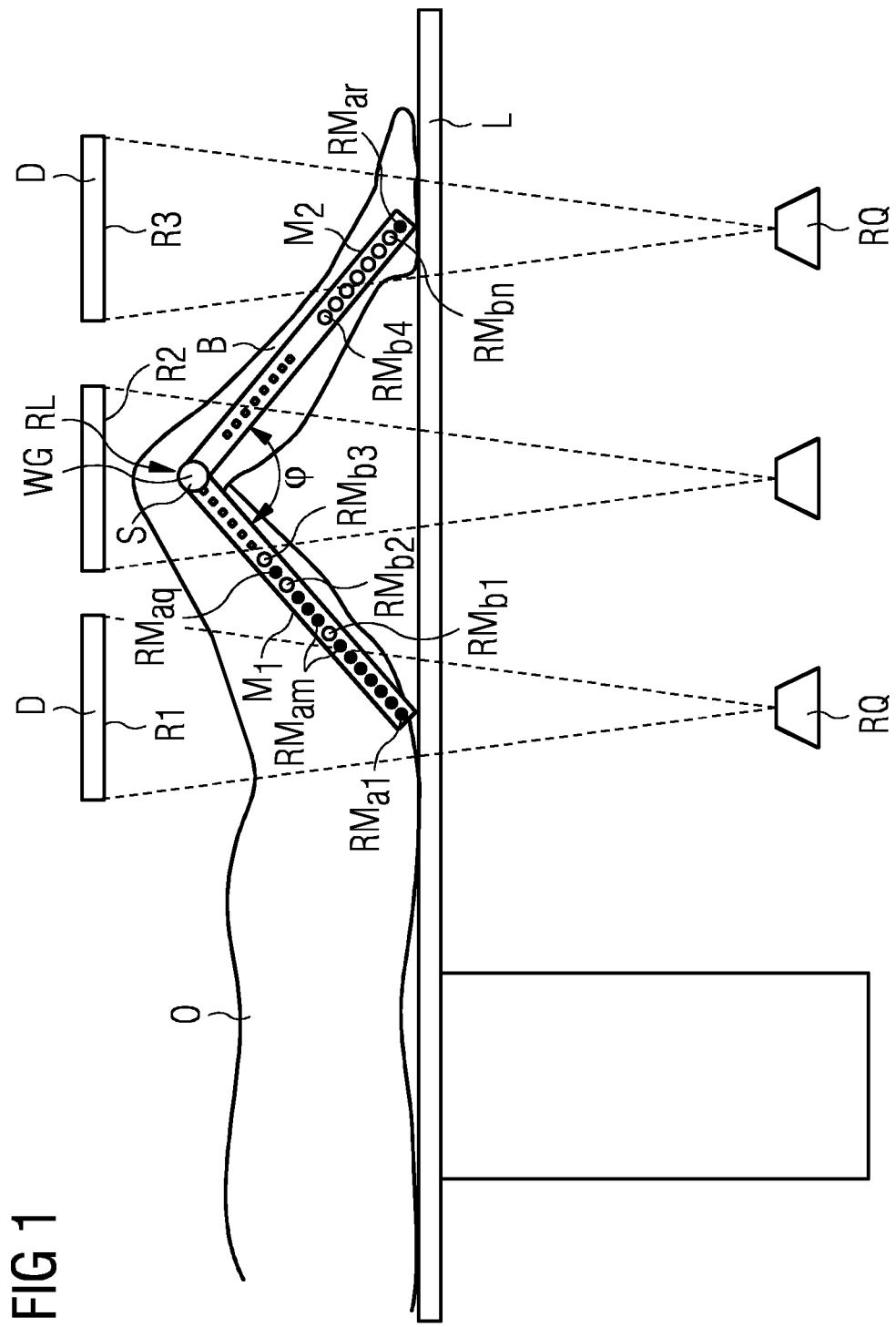
FIG. 1 is a diagrammatic, side view of an x-ray ruler and an n-th time use of an x-ray unit according to the invention.

FIG. 1 schematically images an object O arranged on a table or couch L. Parts of the object O reproduce a schematically imaged leg B. The leg B is positioned on the table L, for example angled due to the medical indication. When using the x-ray ruler RL during a surgical intervention, the x-ray ruler RL, packaged in a sterile manner, is laid against the stretched out or angled leg. The x-ray ruler RL has at least one connection element S. The connection element S can be embodied as a hinge with at least one degree of freedom. An x-ray unit, formed from an x-ray source RQ and a detector D, is also shown. In order to establish the alignment or position of the leg B for further surgical interventions, which are to be carried out in a precise manner, the x-ray ruler RL is aligned with the profile of the leg. Thereafter, a first, second and third x-ray recording R1, R2, R3 are preferably made. The first x-ray recording R1 is made of the leg attachment in a region of a hip, the second x-ray recording R2 is made of a knee joint and the third x-ray recording R3 is made of a lower leg with parts of a foot. For the purpose of these x-ray recordings, the x-ray unit is displaced along the object O to be imaged.

In a manifestation shown here, the x-ray ruler RL is subdivided into a first and second part M1, M2. First and second x-ray markers RMax, RMby are arranged along the first and second part M1, M2 of the x-ray ruler RL. The first and second x-ray markers RMax, RMby have a spherical design. By way of example, the first and second x-ray markers RMax, RMby can differ in terms of their diameters and their x-ray beam absorption coefficients.

At least a first type of first x-ray markers RMa is integrated into the first part M1 of the x-ray ruler RL and at least a second type of second x-ray markers RMb is integrated into the second part M2 of the x-ray ruler RL. In the embodiment of the x-ray ruler RL, which can be angled and is formed from the first part M1 and the second part M2, depicted in FIG. 1, the first and second x-ray markers RMa, RMb are arranged aligned next to one another in a defined sequence. The first and second x-ray markers RMa, RMb are arranged next to one another with defined distances therebetween. There can be encoding first by the distances between the x-ray markers, the diameters, the x-ray absorption coefficients or by the shape of the x-ray markers. The angle forming between the first and second part M1, M2 will be referred to as first angle φ in the following text. By way of example, in FIG. 1, the stringing together of the first type of first x-ray markers RMa in the first part M1 of the x-ray ruler RL is interrupted by at least one second x-ray marker RMb of the second type. In the second part M2 of the x-ray ruler RL the stringing together of the second type of x-ray markers RMbn is interrupted by at least one first x-ray marker RMar of the first type.

In the connection element S, the first angle φ emerging between the first and second part M1, M2 of the x-ray ruler RL can be measured using an angle pickup WG integrated into the connection element S. The measurement can be performed automatically or manually. The connection element S can also be set to a specific first angle φ in an automatic or manual manner. The measurement or setting is forwarded to a computer unit REE of the diagnostic unit. The angle φ formed by the connection element S can either:

a) be set, read and entered into the computer unit in a manual manner,
b) be established by a sensor and entered automatically, or else
c) be determined automatically from the inclinations and positions of the adjacent x-ray ruler parts.

The x-ray unit is displaced along the object O, in this case along a leg B to be treated, for the first, second and third x-ray recording R1, R2, R3. Since the position of the femur and the alignment of the tibia or fibula are of interest to the surgeon in this depiction for establishing the leg axis or the angling of the leg, the regions required for this are recorded by the x-ray recordings R1, R2 and R3. In the figure shown, this is the positioning of the first part M1 of the x-ray ruler RL in the region where the leg is attached and the positioning of the end of the second part in the region of the ankle of the leg. The connection element S should be positioned in the region of the knee. In order to enable the positioning of the x-ray ruler in the region of the knee, the lengths of the first and second part M1, M2 can be lengthened or shortened.

Figure 2:
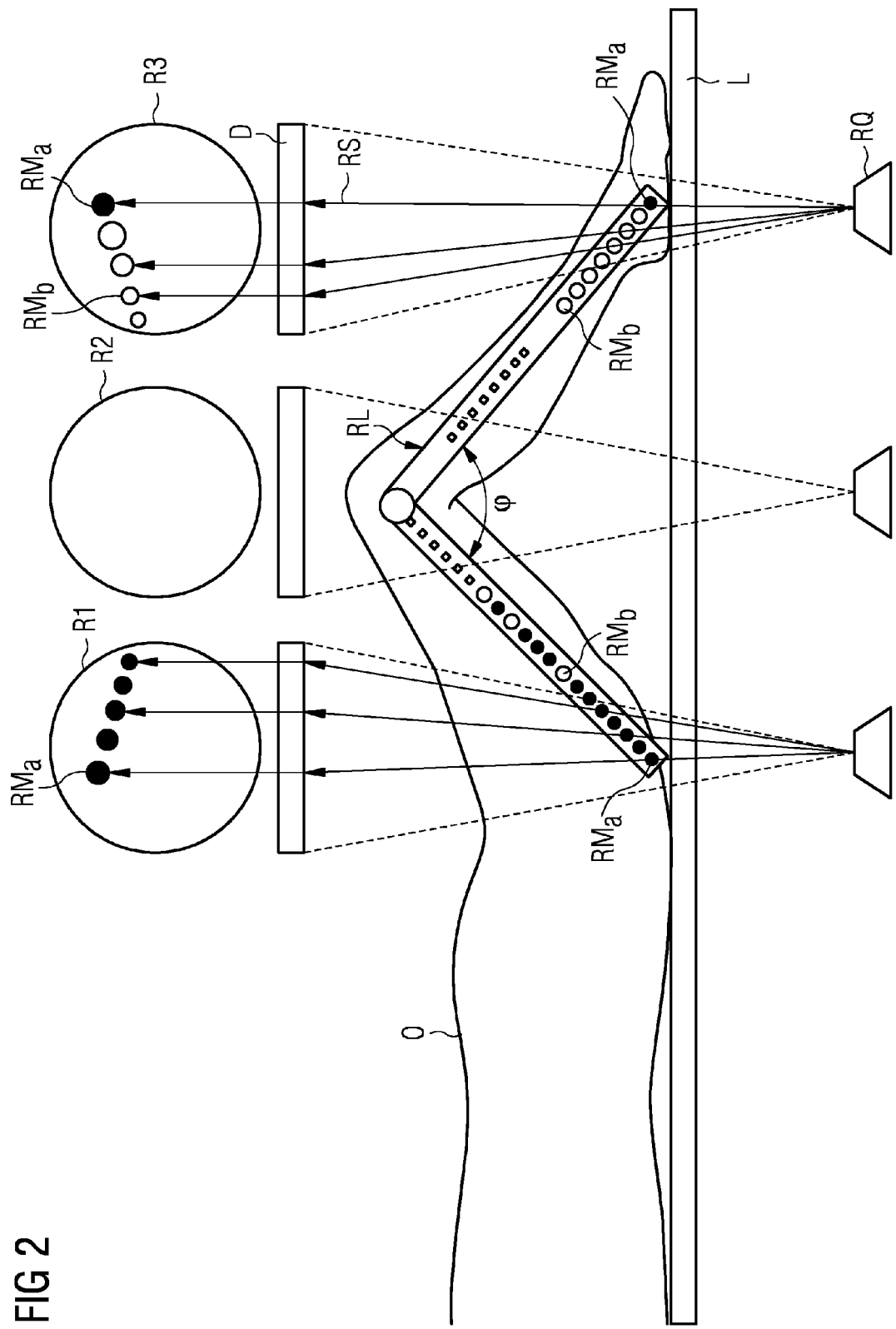
FIG. 2 is an illustration of associated x-ray images with x-ray marker images.

FIG. 2 reproduces the x-ray recordings R1, R2 and R3 for the individual positions of the x-ray unit. The first x-ray recording R1 emerges from a first position of the x-ray unit, the second x-ray recording R2 emerges from a second position of the x-ray unit and the third x-ray image R3 emerges from a third position of the x-ray unit. X-ray markers RMan of the first type are imaged in the first x-ray image R1 and x-ray markers RMar, RMbn of the first and second type are imaged in the third x-ray image R3. Depending on the position of the x-ray unit, x-ray markers of the first and second type RMam, RMbl could also be imaged in the first x-ray recording R1. The first and second x-ray markers RMax, RMby imaged in the respective x-ray image are selected in a selection module SM and the position and diameter thereof are established. The orientation of the respective part of the x-ray ruler in space can be established from a connection line constructed from the selected x-ray markers and the established diameters of the x-ray markers. From the size and the direction of the first and/or second type of first and second x-ray markers RMax, RMby imaged in the first and third x-ray image R1, R3, it is additionally possible to determine an inclination angle of the angled x-ray ruler RL in respect of the table L. The inclination angle will be referred to as second angle β in the following text. After segmenting and establishing the size and the profile of the x-ray markers RMax, RMby, the second angle β of the angled x-ray ruler RL in relation to the surface of the table L is/can also be established in addition to the first angle φ.

The distance of the two ends of the x-ray ruler RL lying on the table is established by the assigned computer unit REE by the position of the first and last x-ray marker arranged in the x-ray ruler RL.

Figure 3:
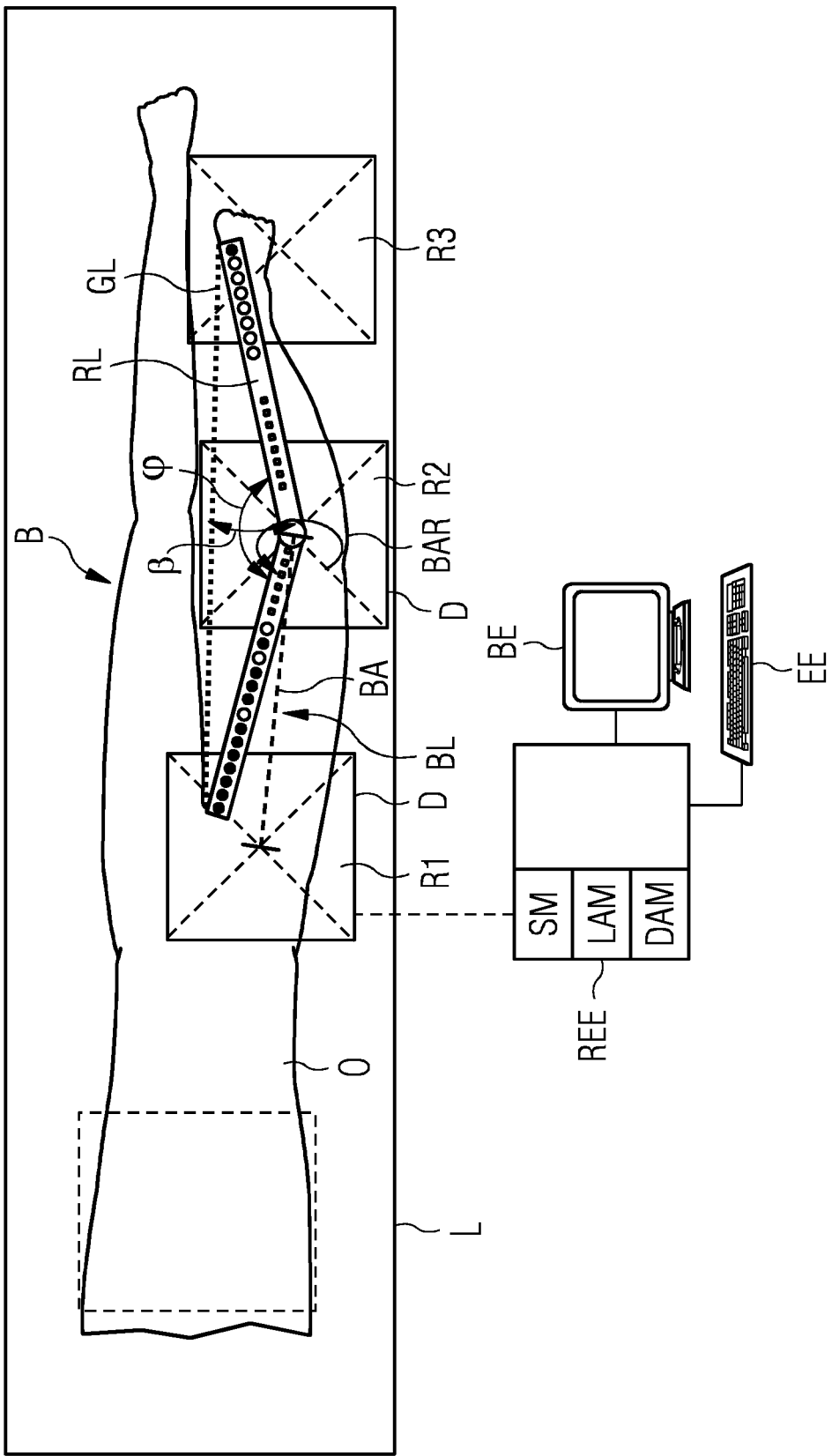
FIG. 3 is a top view of the n-th time use of the x-ray unit.

FIG. 3 reproduces a top view of the n-th time use of the x-ray unit in conjunction with an x-ray ruler RL arranged on an angled leg B. The depicted right angles first reproduce the position of the detector D of the x-ray unit and second reproduce the position of the x-ray images R1, R2 and R3. In addition to the calculation of the alignment, the depicted computer unit REE with monitor unit BE and input unit EE also enables the 3D display of the x-ray ruler RL, the object lengths BL or leg axes BA, for example projected into the x-ray images, on the monitor unit BE.

By means of the different x-ray absorption coefficients and/or different diameters of the conical first and second x-ray markers RMa, RMb, it is possible to reproduce unique bit-patterns on the individual sections of the x-ray ruler RL in the x-ray image, and these bit patterns can be established by image identification algorithms. The x-ray ruler RL, used in the depicted exemplary embodiment, for example has a first and second part M1, M2 with different bit patterns. The first angle φ between the first and second part M1, M2 of the x-ray ruler RL can, firstly, be queried automatically by a sensor in an angle sensor arranged in the connection element S or stored in the computer unit REE calculating the alignment of the x-ray ruler RL. The connection element S can also be embodied in such a way that a predeterminable first angle φ can be set automatically by an input unit. The submodules, reproduced in FIG. 4, for determining the alignment of the x-ray ruler RL which can be angled are reproduced in the computer unit REE.

The modules SM, LAM, DAM, shown in FIG. 4, and the submodules ASM, DEM, GEM, ESEM, ZSEM, EW, ZW; AZM, BL, BA, BAR assigned to the modules reproduce the required hardware and the method steps for stringing together x-ray images and for establishing object data such as e.g. object length and/or object alignment.

After segmenting the x-ray markers in a segmentation module SM of the computer unit REE, the size of the imaged x-ray markers is established. The gradient of the x-ray markers arranged in a line in the x-ray ruler RL can be calculated from the location and the known size of the x-ray markers RMax, RMby integrated into the x-ray ruler RL. As a result of the size of the imaged x-ray markers, the gradient of the first and second part of the x-ray ruler RL can be calculated. As a result of the alignment or the profile of the x-ray markers, it is possible to establish the inclination of the x-ray ruler RL, which can be angled and is placed against the leg B. After the locations of the endpoints of the x-ray ruler RL were established and the further limbs of the imaged x-ray ruler RL were formed from the selected x-ray markers, the tilt of the angled x-ray ruler RL, and hence the 3D geometry of the whole x-ray ruler RL, can be calculated. When evaluating the alignment of the first and second part of the x-ray ruler RL, the arrangement of the first and second type of x-ray markers provides information relating to the direction in which the first and second part of the x-ray ruler extends and where the connection element S is situated. It is possible to identify bit patterns in the individual x-ray images and the 3D position and location of the x-ray ruler can be determined from the measured positions and the size of the spheres and hence the positions of the individual x-ray images can be determined to form an overview or overall x-ray image. The submodule for forming the overview image has not been explicitly depicted. In accordance with FIG. 3, the overview image can be embodied in conjunction with a schematic image of the object to be imaged in the background. The respective leg length BL, leg axis BA and leg rotation BAR can also be inserted into the overview image.

In a first step, the x-ray ruler RL is aligned in an angled manner on the anatomy or position or location of the object O—a leg B in the considered example. It goes without saying that the x-ray ruler RL is placed against or on the object O in a sterile state or in a manner surrounded by a sterile, e.g. transparent, plastic film.

In a second step, a plurality of x-ray recordings are made of the leg B with the x-ray ruler RL lying there against. In this case, at least 3 x-ray recordings of the leg B are made. A first x-ray recording R1 is made of the region of the hip, a second x-ray recording R2 is made of the knee and a third x-ray recording R3 is made of the ankle. During the x-ray recordings, the angular and orbital angle of the x-ray unit remains unchanged. A change in the height or the distance of the detector D or of the x-ray source RQ from the object O to be x-rayed can be undertaken and taken into account in the following calculations.

In a first module—a segmentation module SM—first and second x-ray markers RMa, RMb are segmented in the individual x-ray images R1, R2 and R3.

In a second module—a position determination module LAM—the first and second x-ray markers RMa, RMb, which are imaged in the x-ray images R1, R2, R3 and segmented, are used to establish the data for the spatial arrangement of the x-ray markers and further values required for determining the alignment of the object.

In a third module—a representation module DAM—a virtual reproduction of the x-ray ruler RL is calculated on the basis of the spatial arrangement of the segmented first and second x-ray markers RMax, RMby. This virtual reproduction can be imaged on a monitor unit BE. The first part of the x-ray ruler extends parallel to the femur bone and the second part of the x-ray ruler RL extends parallel to the tibia. In the representation module DAM, the data are evaluated and the x-ray images R1, R2, R3 are combined to form an overview image or overall image.

In the following text, the mode of operation of the individual submodules in the position determination module LAM and in the representation module DAM is described.

In the position determination module LAM, there is an alignment module ASM for establishing the alignment of the selected x-ray marker spheres, a diameter establishment module DEM for establishing the diameters of the selected x-ray markers, a baseline establishment module GEM for establishing a baseline GL connecting the two ends of the x-ray ruler RL, a first limb establishment module ESEM for establishing the length and position of the first part M1 of the x-ray ruler RL, a second limb establishment module ZSEM for establishing the length and position of the second part M2 of the x-ray ruler RL, a first angle establishment module EW for establishing a first angle. The first angle is established from the position of the first and second part of the x-ray ruler RL or by querying the angle pickup or the angle sensor WG of the connection element S between the first and second part M1, M2 of the x-ray ruler RL. A second angle establishment module ZW serves to establish a second angle β, which emerges from the inclination of a virtually formed triangle consisting of a connection line between the ends of the x-ray ruler RL and the first and second part M1, M2 of the x-ray ruler RL in relation to the couch area L.

In the representation module DAM, the calculation operations are derived for stringing together or aligning the x-ray images R1, R2, R3 to form an overall image and/or the visualization of the x-ray ruler RL and the axes and lengths of the imaged objects and from the x-ray images. The length and orientation of an upper and lower leg bone can be inserted into the overall image. The evaluation is brought about on the basis of the established 3D geometry of the x-ray ruler RL. The x-ray ruler RL which can be angled also can be used for upper arm and forearm, the spinal column or the hip in an analogous manner to the shown and described example. As already specified above, it is possible to calculate from the established values, from the calculated data, in an object related manner, such as e.g. the leg length BL, leg axis BA and the leg rotation BAR, and these, as such, can be superimposed into the individual x-ray image R1, R2, R3 or into the overview x-ray image.

The invention claimed is:

1. A device for establishing a spatial position of part of an x-ray ruler imaged in at least one x-ray image, the x-ray ruler including at least a first part and a second part having x-ray markers, and the first part and the second part are connected to each other by a connection element, the x-ray ruler being attached to an alignment of an object to be x-rayed, the device comprising:

a position determination module for determining a spatial configuration of the x-ray markers on a basis of images of the x-ray markers in the x-ray image or x-ray images; and angle sensors disposed in the connection element.

2. The device according to claim 1, further comprising a segmentation module for segmenting the x-ray markers.

3. The device according to claim 1, further comprising a representation module for combining the x-ray images to form an overview image and for a spatial reconstruction of the x-ray ruler on a basis of the spatial configuration of the x-ray markers.

4. The device according to claim 3, wherein said representation module is provided with submodules for displaying an object length, an object alignment and axis profiles of the object and/or of parts of the object.

5. A method for establishing a spatial position of part of an x-ray ruler imaged in at least one x-ray image, which comprises the steps of:

providing a device according to claim 1;

attaching the X-ray ruler to an alignment of an object to be x-rayed, the X-ray ruler having at least a first part and a second part each with x-ray markers, and the first and second parts connected to each other by a connection element; and determining a spatial arrangement of the x-ray markers on a basis of images of the x-ray markers in the x-ray image or x-ray images.

6. The method according to claim 5, which further comprises:

combining the x-ray images to form an overview image; and determining an object length, an object alignment and axis profiles of the object and/or of parts of the object due to the spatial arrangement of the x-ray markers.

7. An x-ray ruler, comprising:

an x-ray ruler body being subdivided into at least a first part and a second part;

a connection element connecting said first part to said second part; and angle sensors disposed in the connection element.

8. The x-ray ruler according to claim 7, further comprising x-ray markers including at least a first type of x-ray markers and at least a second type of x-ray markers disposed on said x-ray ruler body.

9. The x-ray ruler according to claim 8, wherein said x-ray markers are integrated in said x-ray ruler body in a defined sequence.

* * * * *